United States Patent [19]

Wilkinson

[11] 4,254,106
[45] Mar. 3, 1981

[54] BIOLOGICALLY ACTIVE AMIDES

[75] Inventor: Samuel Wilkinson, Beckenham, England

[73] Assignee: Burroughs Wellcome Co., Research Triangle Park, N.C.

[21] Appl. No.: 74,408

[22] Filed: Sep. 10, 1979

Related U.S. Application Data

[60] Division of Ser. No. 815,774, Jul. 14, 1977, which is a continuation-in-part of Ser. No. 762,529, Jan. 26, 1977, abandoned.

[30] Foreign Application Priority Data

Jan. 26, 1976 [GB] United Kingdom ............... 02900/76
Jan. 26, 1976 [GB] United Kingdom ............... 02901/76
Mar. 3, 1976 [GB] United Kingdom ............... 08481/76
Mar. 3, 1976 [GB] United Kingdom ............... 08402/76
Nov. 23, 1976 [GB] United Kingdom ............... 48821/76

[51] Int. Cl.$^3$ .................... A61K 37/00; C07C 103/52
[52] U.S. Cl. ............................... 424/177; 260/112.5 R
[58] Field of Search .................. 260/112.5 R; 424/177

[56] References Cited

U.S. PATENT DOCUMENTS

| | | | |
|---|---|---|---|
| 4,075,190 | 2/1978 | Sarantakis | 260/112.5 R |
| 4,092,304 | 5/1978 | Jones, Jr. et al. | 260/112.5 R |
| 4,143,032 | 3/1979 | Sarantakis | 260/112.5 R |
| 4,148,785 | 4/1979 | Dheer et al. | 260/112.5 R |
| 4,162,307 | 7/1979 | Wilkinson | 260/112.5 R |

*Primary Examiner*—Delbert R. Phillips
*Attorney, Agent, or Firm*—Donald Brown

[57] ABSTRACT

The present invention provides novel peptides of formula (I):

$$R-(X^1)_m-(X^2)_n-X^3-X^4-X^5-X^6-X^7-(X^8)_p-(X^9)_q-R^1 \quad (I)$$

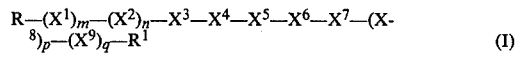

together with their salts, esters, amides, N-alkylamides and N,N-dialkylamides and acid addition salts thereof.

These compounds exhibit morphine agonist activity in both in vitro and in vivo tests and may be used in the treatment of mammals in the fields of both human and veterinary medicine in any condition where an agent with a morphine-like effect is indicated.

28 Claims, No Drawings

BIOLOGICALLY ACTIVE AMIDES

This is a division of application Ser. No. 815,774 filed July 14, 1977, which is a continuation-in-part of application Ser. No. 762,529 filed Jan. 26, 1977 now abandoned.

This invention relates to peptides and derivatives thereof; to the preparation of such compounds; to formulations containing such compounds and the preparation of such formulations; and to the use of the compounds in human and veterinary medicine.

More particularly the present invention relates to peptides and derivatives thereof which exhibit morphine agonist activity. As generally accepted and as the term is used herein, a morphine agonist is a compound the biological activity of which mimics that of the natural alkaloid.

The pharmacological properties and therapeutic uses of morphine are well documented in the literature, see for example "*The Pharmacological Basis of Therapeutics*", Goodman, L. S. and Gilman, A. eds., published by The MacMillan Company, New York, third edition (1965) especially at Chapter 15, pages 247 to 266, and "*Martindale: The Extra Pharmacopoeia*", Blacow, N. W. ed., published by The Pharmaceutical Press, London, twenty-sixth edition (1972) especially at pages 1100 to 1106, all of which is incorporated herein by reference hereto. As is well known however (Goodman, L. S. et al., loc. cit, Chapter 16) repeated administration of morphine can lead to the recipient developing an addition to the drug and tolerance to its effects and to his manifesting withdrawal symptoms when administration is discontinued. For many years therefore research has been conducted with the aim of obtaining a compound having the activity spectrum of morphine while lacking its disadvantages.

The present invention provides the novel peptides of formula (I):

$$R-(X^1)_m-(X^2)_n-X^3-X^4-X^5-X^6-X^7-(X^8)_p-(X^9)_q-R^1 \quad (I)$$

together with their salts, esters, amides, N-alkylamides and N,N-dialkylamides and acid addition salts thereof, which compounds exhibit morphine agonist activity in both in vitro and in vivo tests.

In formula (I):

$X^1$ and $X^2$ are the same or different and each is the radical of a basic amino acid (D or L);

$X^3$ is a D or L radical having the formula:

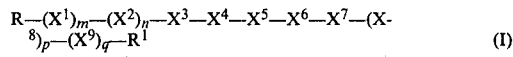

wherein $R^2$ is phenyl or 1,4-cyclohexadien-1-yl, a is 0, 1 or 2, b is 0 or 1, one of W and $W^1$ is a group $-NR^3-$ and the other is hydrogen, provided that W is always $-NR^3-$ when b is 0 and that when $R^2$ is 1,4-cyclohexadien-1-yl a is always 1 and b is always 0, where $R^3$ is hydrogen or a group selected from alkyl, alkenyl, alkynyl, carboxyalkyl, carboxyalkenyl and carboxyalkylnyl, and where $R^2$ is optionally substituted by one or more groups each selected from hydroxy, alkoxy, alkanoyloxy, alkyl, nitro, trifluoromethyl, amino, N-alkylamino, halogen, N,N-dialkylamino and benzyloxy wherein the phenyl ring is optionally substituted by one or more groups each selected from hydroxy, alkoxy, alkanoyloxy, halogen, alkyl, nitro, trifluoromethyl, amino, N-alkylamino and N,N-dialkylamino;

$X^4$ and $X^5$ are the same or different and each is glycyl or a D or L radical selected from C-propargylglycyl, alanyl, α-alkyl alanyl, β-alanyl, valyl, norvalyl, leucyl, isoleucyl, norleucyl, prolyl, hydroxyprolyl, tryptophyl, asparaginyl and glutaminyl, where each of said radicals is optionally $N^2$-substituted with an alkyl group;

$X^6$ is selected from glycyl, a D or L radical selected from methionyl, leucyl, isoleucyl, norleucyl, valyl, norvalyl, prolyl, hydroxyprolyl, alanyl and histidyl, and the values recited hereinabove for $X^3$;

$X^7$ is a D or L radical selected from seryl, homoseryl, O-alkyl seryl, O-alkyl homoseryl, threonyl, O-alkyl threonyl, methionyl sulphoxide, methionyl sulphone, β-homovalyl, homoleucyl, β-homoleucyl, S-methylhomocysteinyl, homomethionyl, β-homomethionyl and the values recited hereinabove for $X^6$;

$X^8$ is selected from the radical of a basic amino acid (D or L) and a D or L radical selected from seryl, threonyl, phenylalanyl and tyrosyl;

$X^9$ is selected from glycyl, the radical of a basic amino acid (D or L), and a D or L radical selected from seryl and threonyl;

R is selected from hydrogen, aralkyl, alkyl, alkenyl, alkynyl, carboxyalkyl, carboxyalkenyl and carboxyalkynyl;

$R^1$ represents the hydroxyl of the 1-carboxyl group of the C-terminal amino acid residue or a group, replacing said 1-carboxyl group, selected from $-CH_2OR^4$, where $R^4$ is hydrogen or alkanoyl, and 5-tetrazolyl optionally substituted in the 1- or 2-position with a group selected from alkyl and benzyl; and m, n, p and q are each selected from 0 and 1, except for the peptides of the formula:

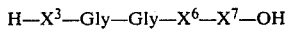
$$H-X^3-Gly-Gly-X^6-X^7-OH$$

and their salts, esters, amides, N-alkylamides and N,N-dialkylamides and acid addition salts thereof, wherein $X^7$ is selected from L-leucyl and L-methionyl and either $X^3$ is selected from L-tyrosyl and L-3,5-diiodotyrosyl and $X^6$ is L-phenylalanyl, or $X^3$ is L-tyrosyl and $X^6$ is L-4-chlorophenylalanyl.

The abbreviations used herein for amino acids and their radicals are those conventional in the art and may be found in, for example, *Biochemistry*, 11, 1726 (1972). In the above and throughout the following all references are to the L-amino acids and their radicals except in the case of glycine and unless otherwise stated.

By the term "basic amino acid" is herein meant an amino acid having two basic functions and one carboxyl group, and as examples of the radicals $X^1$, $X^2$, $X^8$ and $X^9$ may be mentioned lysyl (D and L), homoarginyl (D and L), ornithyl (D and L), histidyl (D and L), α,γ-diaminobutyryl (D and L) and arginyl (D and L).

In formula (I), the optional alkyl substituents of the radicals $X^4$ and $X^5$, the alkyl moiety of the α-alkyl alanyl identity for $X^4$ and $X^5$ and the alkyl moiety of the O-alkyl seryl, O-alkyl homoseryl and O-alkyl threonyl identifies for $X^7$ desirably have 1 to 4 and preferably 1 or 2 carbon atoms. In the phenyl or 1,4-cyclohexadien-1-yl ring $R^2$ of the radical $X^3$, and in the optional benzyloxy substituents therein, the optional halogen substituents may be selected from fluorine, chlorine, bromine and iodine and the optional alkyl and alkoxy substituents together with the alkyl moieties of the optional alkanoyloxy, N-alkylamino and N,N-dialkylamino substituents desirably have 1 to 4 and preferably 1 or 2 carbon atoms.

When the phenyl or cyclohexadien-1-yl ring of the radical $X^3$ has 1 or 2 substituent groups thereon said groups are desirably located at the 3- and/or 4-position(s) of the said ring.

The alkyl identity for R and for the group $R^3$ of the radical $X^3$ together with said moiety in the carboxyalkyl identity therefor may in particular have 1 to 4 carbon atoms, for example 1 or 2, but such groups having for example 1 to 10 or 1 to 20 carbon atoms are to be understood as also included. The alkenyl and alkynyl identifies for R and $R^3$ together with said moieties in respectively the carboxyalkenyl and carboxyalkynyl identifies therefor may in particular have 2 to 4 carbon atoms but such groups having for example 2 to 10 or 2 to 20 carbon atoms are to be understood as within the scope of formula (I). As particular values for said alkenyl and alkynyl groups respectively may be mentioned allyl ($\alpha$, $\beta$ or $\gamma$) and propargyl.

When R is aralkyl this may be for example benzyl optionally substituted in the phenyl ring by one or more groups each selected from those recited hereinbefore in respect of the optional benzyloxy substituent of the group $R^2$ in the radical $X^3$.

When $R^1$ is a group —$CH_2OR^4$ wherein $R^4$ is alkanoyl the alkyl moiety of said alkanoyl group desirably has 1 to 4 and preferably 1 or 2 carbon atoms. When $R^1$ is 5-tetrazolyl the optional alkyl substituent thereon desirably has 1 to 5 carbon atoms and the optional benzyl substituent thereon is itself optionally substituted in the phenyl ring by one or more groups each selected from those recited hereinbefore in respect of the optional benzyloxy substituent of the group $R^2$ in the radical $X^3$.

Among the esters of the peptides of formula (I) may be mentioned the alkyl esters and the aryl esters. The alkyl esters include in particular those wherein the alkyl group has 1 to 4 carbon atoms, for example the methyl, ethyl and t-butyl esters, but esters wherein the alkyl group has for example 1 to 10 or 1 to 20 carbon atoms are to be understood as also included. The aryl esters include phenyl esters, for example halophenyl esters where the halo is for example chloro as in p-chlorophenyl.

In the N-alkyl- and N,N-dialkylamides of the peptides of formula (I) the alkyl groups may in particular have 1 to 5 carbon atoms but alkyl groups having for example 1 to 10 or 1 to 20 carbon atoms are to be understood as also included and in the N,N-dialkylamides the alkyl groups may be the same or different. The amides of the peptides should be understood to include those notionally derived not only from ammonia but also from heterocyclic bases such as pyrrolidine, piperidine and morpholine, that is to say, the pyrrolidineamides, piperidineamides and morpholineamides respectively.

Thus a sub-class of the amides, N-alkylamides and N,N-dialkylamides of the peptides of formula (I) may be represented by the formula:

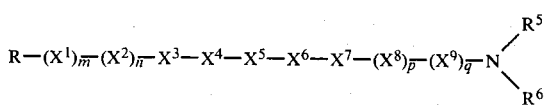

wherein $X^1$, $X^2$, $X^3$, $X^4$, $X^5$, $X^6$, $X^7$, $X^8$, $X^9$, m, n, p, q and R have the meanings as hereinabove recited in formula (I) and $R^5$, $R^6$ and the nitrogen atom to which they are attached together comprise a group selected from amino, pyrrolidino, piperidino, morpholino, N-alkylamino and N,N-dialkylamino where the "alkyl" in each instance has 1 to 20 carbon atoms.

In the acid addition salts of the peptides of formula (I) and of their derivatives as hereinabove recited the activity resides in the base and the acid is of less importance although for therapeutic purposes it is preferably pharmacologically and pharmaceutically acceptable to the recipient. Examples of such suitable acids include (a) mineral acids: hydrochloric, hydrobromic, phosphoric, metaphosphoric, nitric and sulphuric acids; (b) organic acids: tartaric, acetic, citric, malic, lactic, fumaric, benzoic, glycollic, gluconic, gulonic, succinic and arylsulphonic, for example p-toluenesulphonic, acids. The pharmaceutically and pharmacologically acceptable acid addition salts together with those salts which are not so acceptable (for example salts of hydrofluoric and perchloric acids) have utility in isolation and purification of the bases, and of course the unacceptable salts are also valuable in the preparation of the acceptable salts by techniques well known in the art. Those peptides and their derivatives containing a plurality of free amino groups may be obtained in the form of mono- or poly-acid addition salts, or as mixed salts of a plurality of acids.

Likewise in the salts of the peptides (comprising the peptide as the carboxylate anion together with a cation) the identity of the cation is of less importance although for therapeutic purposes it is preferably pharmacologically and pharmaceutically acceptable to the recipient. Examples of such suitable cations include sodium and potassium.

Included among the novel peptides of formula (I) are the peptides of the formula:

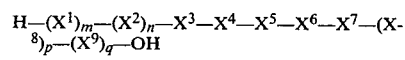

together with their salts, esters, amides, N-alkylamides and N,N-dialkylamides and acid addition salts thereof, wherein $X^1$ and $X^2$ are the same or different and each is the radical of a basic amino acid (D or L);

$X^3$ is selected from phenylalanyl (D or L) and C-phenylglycyl (D or L), where each of said groups is optionally $N^2$-substituted with an akyl group and is optionally substituted in the 3- and/or 4- position of the phenyl ring by a group(s) each selected from hydroxy, alkoxy, acyloxy and benzyloxy;

$X^4$ is selected from glycyl, alanyl (D or L), valyl (D or L), norvalyl (D or L), leucyl (D or L), isoleucyl (D or L), norleucyl (D or L), propyl (D or L) and hydroxyprolyl (D or L), where each of said groups is optionally $N^2$-substituted with an alkyl group;

$X^5$ is selected from asparaginyl (D or L), glutaminyl (D or L), where each of said groups is optionally $N^2$-substituted with an alkyl group, and the values recited hereinabove for $X^4$;

$X^6$ is selected from methionyl (D or L), leucyl (D or L), isoleucyl (D or L), norleucyl (D or L), valyl (D or L), norvalyl (D or L), prolyl (D or L), hydroxyprolyl (D or L), glycyl, alanyl (D or L) and the values recited hereinabove for $X^3$;

$X^7$ is selected from methionyl (D or L), seryl (D or L), threonyl (D or L), leucyl (D or L), isoleucyl (D or L), norleucyl (D or L), valyl (D or L), norvalyl (D or L), prolyl (D or L), hydroxyprolyl (D or L), glycyl, alanyl (D or L) and the values recited hereinabove for $X^3$;

$X^8$ and $X^9$ are the same or different and each is selected from seryl (D or L) and threonyl (D or L); and m, n, p and q are each selected from 0 and 1, provided that, when m, n, p and q are all 0 and $X^3$, $X^4$, $X^5$ and $X^6$ are respectively tyrosyl, glycyl, glycyl and phenylalanyl, then $X^7$ is other than methionyl or leucyl.

Also included among the novel peptides of formula (I) are the peptides of the formula:

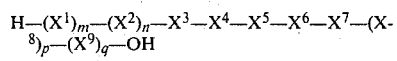

together with their salts, esters, amides, N-alkylamides and N,N-dialkylamides and acid addition salts thereof, wherein $X^1$ and $X^2$ are the same or different and each is the radical of a basic amino acid;

$X^3$ and $X^6$ are the same or different and each is selected from phenylalanyl and C-phenylglycyl, where each of said groups is optionally N-substituted by an alkyl group and is optionally substituted in the 3- and/or 4-position of the phenyl ring by a group(s) each selected from hydroxy, alkoxy, acyloxy and benzyloxy;

$X^4$ and $X^5$ are the same or different and each is selected from glycyl, alanyl (D or L), valyl (D or L), norvalyl (D or L), leucyl (D or L), isoleucyl (D or L), norleucyl (D or L), prolyl (D or L) and hydroxyprolyl (D or L), where each of said groups is optionally N-substituted by an alkyl group;

$X^7$ is selected from methionyl, leucyl, isoleucyl, norleucyl, valyl, norvalyl, prolyl, hydroxyprolyl, glycyl, alanyl and the values recited hereinabove for $X^3$ and $X^6$;

$X^8$ and $X^9$ are the same or different and each is selected from seryl and threonyl; and m, n, p and q are each selected from 0 and to 1, provided that, when m, n, p and q are all 0 and $X^3$, $X^4$, $X^5$ and $X^6$ are respectively tyrosyl, glycyl, glycyl and phenylalanyl, then $X^7$ is other than methionyl or leucyl.

The morphine agonist properties of the peptides of formula (I) and their derivatives as hereinbefore defined include the following, which are given solely by way of illustration and should be understood to be non-limiting.

(A) In vitro (i) Inhibition of neurally evoked contractions of the isolated mouse vas deferens when tested by the method of Huges et al. (*Brain Research,* 88 (1975) 296) (using pulses at 0.1 Hz), the inhibition being abolished by the known narcotic antagonist naloxone (1-N-allyl-7,8-dihydro-14-hydroxy normorphinone).

(ii) Reduction of electrically-induced contractions of the isolated guinea-pig ileum when prepared for stimulation after the manner of Paton (*Brit. J. Pharmacol.,* 12 (1957) 119–127). (Each intestinal segment was impaled by the anode and suspended with a 2–3 g load. Stimulus parameters: frequency: 0.1 Hz: duration: 0.4 ms; voltage (supramaximal) 30–40 V; the contractions were transduced isotonically).

(B) In vivo (i) The compounds exhibit analgesic activity, for example they are effective in reducing phenylbenzoquinone-induced writhing in mice when tested by a modification of the method of Hendershot et al. (*J. Pharm. exp. Therap.,* 125 (1959) 237) (the compounds being administered by intracerebroventricular injection) and this reduction is abolished by naloxone.

(ii) The compounds exhibit antitussive activity, for example when tested in guinea-pigs according to the method of Boura et al. *Brit. J. Pharmacol,* 39 (1970) 225.

(iii) The compounds exhibit antidiarrhoeal activity, for example they are effective in reducing castor oil-induced diarrhoea in rats.

As subclasses of the peptides of formula (I) and their derivatives may be mentioned those compounds wherein:

(i) m and n are both 0;
(ii) p and q are both 0;
(ii) $X^3$ is L-tyrosyl;
(iv) $X^4$ is the radical of a D-amino acid, preferably D-alanine;
(v) $X^5$ is glycyl;
(vi) $X^6$ is L-phenylalanyl;
(vii) $X^7$ is the radical of a D-amino acid, preferably D-leucine or D-methionine.

As a further subclass may be mentioned those peptides and their derivatives of the formula:

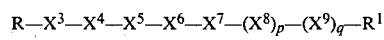

wherein R, $R^1$, p and q are as defined in formula (I);

$X^3$ is L-tyrosyl, $O^{4'}$-acetyl-L-tyrosyl or N-methyl-L-tyrosyl;

$X^4$ is glycyl, L-alanyl, α-methyl-alanyl or D-alanyl;

$X^5$ is glycyl, sarcosyl or L-asparaginyl;

$X^6$ is L-phenylalanyl, L-tyrosyl or L-4-chlorophenylalanyl;

$X^7$ is L-leucyl, D-leucyl, L-methionyl, D-methionyl, L-norleucyl, L-threonyl or D-β-homoleucyl;

$X^8$ is L-threonyl, D-threonyl, L-phenylalanyl, L-tyrosyl or L-lysyl; and $X^9$ is glycyl or L-lysyl.

As a yet further subclass may be mentioned those peptides and their derivatives of the formula:

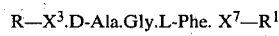

wherein R and $R^1$ are as defined in formula (I);

$X^3$ is L-tyrosyl or N-methyl-L-tyrosyl; and $X^7$ is D-leucyl or D-methionyl.

The peptides of formula (I) and their derivatives as hereinabove recited may be prepared by any of the methods known in the art for the preparation of compounds of analogous structure. Thus they may be formed by the sequential coupling of appropriate amino acids using either classical methods of peptide synthesis or solid phase procedures, or by the initial preparation and subsequent coupling of peptide subunits.

Such reactions may be effected by, for example, activating the carboxylic acid group of the ingoing amino acid and protecting the non-reacting amino and carboxylic acid groups. Such techniques are standard in the peptide art. Details of suitable activating and protecting (masking) groups and of suitable reaction conditions (both for the coupling reactions and for the removal of protecting groups) giving the minimum of racemisation may be found in the following literature, all of which is incorporated herein by reference hereto, which is given purely by way of exemplification and which is intended to be neither exhaustive nor limiting.

(a) Published United Kingdom patent application Nos. 1 042 487; 1 048 086; and 1 281 383.

(b) Schröder and Lüebke, "*The Peptides*" (Academic Press) (1965).
(c) Bellean and Malek, *J. Am. Chem. Soc.*, 90, 165(1968).
(d) Tilak, *Tetrahedron Letters*, 849 (1970).
(e) Beyerman, *Helv. Chim. Acta.*, 56, 1729 (1973).
(f) Stewart and Young, "*Solid Phase Peptide Synthesis*" (W. H. Freeman and Co.) (1969).

Depending upon the reaction conditions the peptides of formula (I) and their derivatives are obtained in the form of the free base or as an acid addition salt thereof or (in the case of the peptides themselves) as a salt thereof. The acid addition salts may be converted into the free bases or salts of other acids, and the bases may be converted into acid addition salts thereof, by techniques well known in the art. Likewise the peptides may be converted to salts thereof, and the salts converted to the peptides or to other salts, by well established techniques.

The peptides of formula (I) and their derivatives as hereinabove recited and acid addition salts thereof may thus be prepared by condensing a reagent (II)

$$R—Y^1—OH \qquad (II)$$

wherein $Y^1$ is selected from the radical $(X^1)_m$ as defined in formula (I) and a partial radical sequence having the radical $(X^1)_m$ at its N-terminal end and from thereon corresponding to formula (I), with a reagent (III)

$$H—Y^2 \qquad (III)$$

wherein $Y^2$ corresponds to the balance of the above defined product, the reagents (II) and (III) being optionally protected and/or activated where and as appropriate; followed if necessary and as appropriate by one or both of the steps of deprotection of the product and conversion of the product into the base or a salt or an acid addition salt thereof.

With regard to the peptides of formula (I) and their derivatives wherein the radical $X^7$ is methionyl (D or L), the reagent (II) identified above desirably corresponds to the N-terminal fragment thereof having either (i) the methionyl radical $X^7$ in the C-terminal position, the reagent (III) then having the radical $(X^8)_p$ in the N-terminal position, or (ii) the radical $X^6$ in the C-terminal position, the reagent (III) then having the methionyl radical $X^7$ in the N-terminal position, and for general convenience the former possibility is preferred.

It will be appreciated by those skilled in the peptide art that the arginyl (D or L) and homoarginyl (Har) (D or L) radicals may not only be incorporated into the peptide chain in the fashion described above but may also be formed in situ in the assembled chain, or in a subunit thereof, by guanidation of an ornithyl (D or L) or lysyl (D or L) radical respectively, using a reagent such as 1-guanyl-3,5-dimethylpyrazole.

It will also be appreciated that other in situ conversions of the peptides of formula (I) and their derivatives are possible. Thus the amides, N-alkylamides and N,N-dialkylamides may be prepared by for example reaction of a peptide alkyl ester such as the methyl esster with ammonia, a heterocyclic base or a mono- or dialkylamine, as appropriate. The peptide esters may be prepared from the peptides by standard esterification procedures and the esters may be converted to the peptides by saponification. Substituent hydroxy group(s) in the group $R^2$ of the radical $X^3$ may be converted to alkoxy or benzyloxy groups by the use of the appropriate diazoalkane, for example diazomethane to provide methoxy groups. Substituent benzyloxy and alkanoyloxy group(s) in the group $R^2$ of the radical $X^3$ may be removed to leave hydroxy groups by hydrogenolysis in methanol using 10% palladium on charcoal catalyst and by alkaline hydrolysis respectively, and the hydroxy group(s) may be converted to alkanoyloxy groups by standard alkanoylation procedures. All these are conventional techniques in the peptide art and reference may be made to the literature referred to hereinabove for details of reaction conditions and of appropriate protection/deprotection procedures.

Because of their morphine agonist activity already alluded to the peptides of formula (I) together with their pharmacologically and pharmaceutically acceptable salts, esters, amides, N-alkylamides and N,N-dialkylamides and pharmacologically and pharmaceutically acceptable acid addition salts thereof may be used in the treatment of mammals in the fields of both human and veterinary medicine in any condition where an agent with a morphine-like effect is indicated. Specific utilities that may be mentioned, by way of example, include the following:

(1) The relief of pain (analgesia), for example pain arising from spasm of smooth muscle as in renal or biliary colic, pain due to terminal illness such as cancer, pain in the post-operative period, and obstetrical pain.

(2) Sedation, for example in pre-anaesthetic medication; tranquilization; the induction of sleep, especially where sleeplessness is due to pain or cough; and the relief of anxiety in general.

(3) The suppression of cough.

(4) The relief of dyspnoea, for example that of acute left ventricular failure or pulmonary oedema.

(5) The induction of constipation, for example after ileostomy or colostomy, and the treatment of diarrhoea and dysentery.

(6) The induction of euphoria and the treatment of depression, for example when allied to the relief of pain in terminal illness such as cancer.

For each of these utilities the amount required of the peptide or derivative thereof or acid addition salt thereof (hereafter referred to as the active ingredient) will vary with the route of administration and with the severity of the condition to be treated, and will ultimately be at the discretion of the physician or veterinarian. In general however for each of these utilities the dosage will be in the range 0.0025μg. to 40 mg. per kilogram body-weight of mammal, preferably 0.025 μg. to 4.0 mg./kg., and optionally 0.25 to 400 μg./kg. (all dosages calculated with references to the peptide base).

The active ingredients may be administered by any route appropriate to the condition to be treated, suitable routes including oral, rectal, nasal, topical (buccal), vaginal and parenteral (including subcutaneous, intramuscular and intravenous). It will be appreciated that the preferred route will vary with the condition to be treated and thus for example in the relief of obstetrical pain administration directly into the spinal cord may be advantageous.

While it is possible for the active ingredients to be administered as the raw chemical it is preferable to present them as a pharmaceutical formulation preparation.

The formulations, both veterinary and for humen use, of the present invention comprise an active ingredient, as above defined, together with one or more acceptable carriers therefor and optionally other therapeutic ingredients. The carrier(s) must be "acceptable" in the sense of being compatible with the other ingredients of the formulats on and not deleterious to the recipient thereof. Desirably the formulations should not include oxidising agents and other substances with which peptides are known to be incompatible.

The formulations include those suitable for oral, rectal, nasal, topical (buccal), vaginal or parenteral (including subcutaneous, intramuscular and intravenous) administration, although the most suitable route in any given case will depend upon for example the active ingredient and the condition to be treated. The formulations may conveniently be presented in unit dosage form and may be prepared by any of the methods well known in the art of pharmacy. All methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product into the desired formulation.

Formulations of the present invention suitable for oral administration may be presented as discrete units such as capsules, cachets or tablets each containing a predetermined amount of the active ingredient; as a powder or granules; or as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine, the active ingredient in a free-flowing form such as a powder or granules, optionally mixed with a binder, lubricant, inert diluent, lubricating, surface active or dispersing agent. Moulded tablets may be made by moulding in a suitable machine, a mixture of the powdered compound moistened with an inert liquid diluent.

Formulations for rectal administration may be presented as a suppository with the usual carriers such as cocoa butter, while a suitable formulation for nasal administration is nasal drops comprising the active ingredient in aqueous or oily solution.

Formulations suitable for topical administration in the mouth include lozenges comprising the active ingredient in a flavoured basis, usually sucrose and acacia or tragacanth; and pastilles comprising the active ingredient in an inert basis such as gelatin and glycerin, or sucrose and acacia.

Formulations suitable for vaginal administration may be presented as pessaries, creams, pastes or spray formulations containing in addition to the active ingredient such carriers as are known in the art to be appropriate.

Formulations suitable for parenteral administration conveniently comprise sterile aqueous solutions of the active ingredient, which solutions are preferably isotonic with the blood of the recipient. Such formulations may be conveniently prepared by dissolving solid active ingredient in water to produce an aqueous solution, and rendering said solution sterile and isotonic with the blood of the recipient. The formulations may be presented in unit - or in multidose containers, for example sealed ampoules or vials.

Formulations suitable for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose.

It should be understood that in addition to the aforementioned ingredients the formulations of this invention may include one or more additional ingredients such as diluents, buffers, flavouring agents, binders, surface active agents, thickeners, lubricants, preservatives (including anti-oxidants) and the like.

Where the formulation, for human or for veterinary use, is presented in unit dosage form, for example those unit dosage forms specifically mentioned above, each unit thereof conveniently contains the active ingredient (as above defined) in an amount in the range 0.125 $\mu$g. to 2 g., preferably 1.25 $\mu$g. to 200 mg. and optionally 12.5 $\mu$g. to 20 mg. (all weights calculated with reference to the peptide base).

It will be appreciated from the foregoing that what we will claim may comprise any novel feature described herein, principally and not exclusively, for example:

(a) The peptides of formula (I) as hereinabove defined together with their salts, esters, amides, N-alkylamides and N,N-dialkylamides and acid addition salts thereof.

(b) Methods as described herein above for the preparation of the peptides of formula (I) and their derivatives recited in (a) above and acid addition salts thereof.

(c) Pharmaceutical formulations comprising a peptide of formula (I), a pharmacologically and pharmaceutically acceptable salt, ester, amide, N-alkylamide of N,N-dialkylamide thereof or a pharmacologically and pharmaceutically acceptable acid addition salt thereof together with an acceptable carrier therefor.

(d) Methods for the preparation of the pharmaceutical formulations defined in (c) above.

(e) A method for the treatment of a mammal for a condition wherein an agent with a morphine-like effect is indicated, comprising the administration to the mammal of a treatment effective non-toxic amount of a peptide of formula (I), a pharmacologically and pharmaceutically acceptable salt, ester, amide, N-alkylamide or N,N-dialkylamide thereof or a pharmacologically and pharmaceutically acceptable acid addition salt thereof.

(f) A method according to (e) above for the treatment of a condition selected from those specifically identified hereinabove under (1), (2), (3), (4), (5) or (6).

The following Examples serve to illustrate the present invention but should not be construed as in any way providing a limitation thereof. All temperatures are in degrees Celsius.

Experimental Section

The following abbreviations are used throughout
HOBT—1-hydroxybenzotriazole
DCCI—dicyclohexylcarbodiimide
DCU—dicyclohexylurea
NMM—N-methylmorpholine
DMF—dimethylformamide
Pr—isopropanol
Pr$_2$O—diisopropyl ether
pe—petroleum ether
EtOAc—ethyl acetate
Z—benzyloxycarbonyl
Bu—tertiary butyl
BOC—tertiary butyloxycarbonyl
Bzl—benzyl Peptides were examined by tlc on Merck silicagel plates with the following solvent systems:
(1) methylethylketone
(2) n-butanol : acetic acid : water (3:1:1)
(3) chloroform : methanol : 32% acetic acid (12:9:4)
(4) chloroform : methanol : 880 ammonia (12:9:4)
(5) ethylacetate : n-butanol : acetic acid : water (1:1:1:1)
(6) chloroform : methanol (8:1)

All amino acids were of the L-configuration unless otherwise stated.

Optical rotations were determined on a Bendix NPL automatic polarimeter.

The amino acid compositions of peptide hydrolysates (6 N.HCl at 110° for 24 hours in evacuated sealed tubes) were determined with a Beckman-Spinco Model 120C amino acid analyser or with a Rank Chromostak amino acid analyser.

The following general procedures were used throughout the syntheses of the peptides.
(a) Couplings were carried out in DMF and were mediated by DCCI.
(b) Amino acid ester hydrochlorides were converted to the free esters by addition of a tertiary base, either triethylamine or N-methyl morpholine.
(c) HOBT was added at the coupling stage when fragment condensation involved a peptide having an optically active carboxy terminal amino acid e.g. coupling with BOC.Tyr.D-Ala.Gly.Phe.OH.
(d) Couplings were allowed to proceed for 24 hours in the cold room at +4° C.
(e) After coupling, purification was effected by washing with acid and base to remove unchanged reactants.
(f) Alkaline saponifications were carried out in aqueous methanol with an autotitrator at pH 11.5 to 12.0 with N.NaOH.
(g) Benzyloxycarbonyl protecting groups were removed by hydrogenolysis in methanol/acetic acid with 10% palladium on charcoal.
(h) The resulting acetate salts from the above hydrogenolysis were converted to the corresponding hydrochlorides by an addition of methanolic hydrogen chloride.
(i) Benzyl protecting were removed by hydrogenolysis in methanol with 10% palladium on charcoal.
(j) Tertiary butyl and tertiary butyloxycarbonyl protecting groups were removed with N-hydrogen chloride in acetic acid, in the presence of anisole to act as a scavenger. Cleavage was allowed to proceed for 60 to 90 minutes.

OBu protecting groups on the alcoholic functions of threonine and serine were removed with trifluoroacetic acid containing 10% water, cleavage being allowed to proceed for 90 minutes.

(l) The final peptides were isolated as their hydrochlorides and were lyophilised from aqueous solution.

REFERENCE PREPARATION 1

BOC.Tyr.Gly.Gly.Phe.OH

This was prepared according to the scheme set out in Table 1, wherein the various protecting groups have the following identities:
Z: benzyloxycarbonyl
Me: methyl
BOC: t-butyloxycarbonyl All couplings were carried out in dimethylformamide using dicyclohexylcarbodiimide, the reaction mixtures being stirred at 4° C. for a minimum of 24 hours.

The peptide methyl esters (1), (5) were saponified in solution in methanol-water (3:1 v/v) by addition of 2N aqueous sodium hydroxide at pH 11.5 (pH stat). The protecting group Z was cleaved from the protected tripeptide (3) by hydrogenolysis in methanol in the presence of 10% palladium on charcoal catalyst.

Characterising data are set out in Table 2 wherein Rf refers to thin layer chromatography using Merck silica gel and the solvent systems indicated.

TABLE 1

| Tyr | Gly | Gly | Phe |
|---|---|---|---|
| | Z . Gly . OH | H-Gly . OMe | |
| | Z . Gly —(1)— | Gly . OMe | |
| | Z . Gly —(2)— | Gly . OH | H . Phe . OMe |
| | Z . Gly —(3)— | Gly —————— | Phe . OMe |
| BOC . Tyr . OH | H . Gly —(4)— | Gly —————— | Phe . OMe |
| BOC . Tyr ——— | — Gly —(5)— | Gly —————— | Phe . OMe |
| BOC . Tyr ——— | — Gly —(6)— | Gly —————— | Phe . OH |

REFERENCE PREPARATION 2

BOC.Tyr.Gly.Gly.Phe.OH

By the process described in R.P. 1 the compound (4) was prepared and coupled with fully protected tyrosine (Bzl is a benzyl group) as set out in Table 3 to give the protected tetrapeptide (9). This was saponified in the manner described in R.P. 1 to give (10) from which the group Bzl was cleaved by hydrogenolysis in methanol in the presence of 10% palladium on charcoal catalyst.

TABLE 2

| | Rf * | M.p.°C. | Crystallisation Solvent $\phi$ | Elemental analysis |
|---|---|---|---|---|
| (1) | 0.65$^a$ | 66–67 | EtAc/p.e. | $C_{13}H_{16}N_2O_5$ req.: C,55.7; H,5.7; N,10.0 Found C,55.8; H,5.9; N,10.3 |
| (2) | 0.59$^a$ | 180 | sq. EtOH | $C_{12}H_{14}N_2O_5$ req.: C,54.1; H,5.3; N,10.5 Found C,54.3; H,5.6; N,10.4 |
| (3) | 0.40$^b$ | 58 | Ethyl acetate/ diisopropyl ether | $C_{22}H_{25}N_3O_6$ req.: C,61.8; H,5.9; N, 9.8 Found C,61.6; H,5.8; N, 9.6 |
| (4)(N.Cl) | 0.77$^c$ | 182.3 | Methanol/ isopropanol | $C_{14}H_{20}ClN_3O_4$ C,51.0; H,6.1; N,12.8 req.: Found C,51.3; H,6.3; N,12.6 |
| (5) | 0.33$^b$ | | | |

TABLE 2-continued

| Rf* | M.p.°C. | Crystallisation Solvent φ | Elemental analysis |
|---|---|---|---|
| (6) 0.8ᵃ | | | |

*Solvent
(a) n-butanol; acetic acid; water(3:1:1)
(b) methylethyl ketone
(c) chloroform; methanol; 32% acetic acid (12:9:4)
φ p.e. : petroleum ether
EtAc : ethyl acetate
EtOH : ethanol

TABLE 3

| | Tyr | Gly | Gly | Phe |
|---|---|---|---|---|
| BOC . | Tyr . OH | H―Gly | (4) Gly | Phe . OMe |
| | OBzl | | | |
| BOC . | Tyr | Gly | (9) Gly | Phe . OMe |
| | OBzl | | | |
| BOC . | Tyr | Gly | (10) Gly | Phe . OH |
| BOC . | Tyr | Gly | (6) Gly | Phe . OH |

| | Rf* | M.p. and crystallization solvent | Elemental analysis |
|---|---|---|---|
| (9) | 0.83ᵃ | | |
| | 0.34ᵇ | | |
| (10) | 0.70ᵃ | 138.2° C. | C₂₄H₄₀N₄O₈ req.: |
| | 0.06ᵇ | EtAc | C, 64.56; H, 6.33; N, 8.86 |
| | | | Found: |
| | | | C, 64.42; H, 6.46; N, 8.55% |

Characterising data for the intermediates (9) and (10) are as given in Table 3, wherein Rf refers to thin layer chromatography using Merck silica gel and the solvent systems indicated.

EXAMPLES 1 to 3

Peptides of formula: H.Tyr.Gly.Gly.Phe.X⁷.OH

Peptides of this formula were prepared by condensing the protected tetrapeptide BOC.Tyr.Gly.Gly.Phe-OH (Reference Preparations 1 and 2) with a suitably carboxy-protected amino acid derivative H-X⁷-OR

| | Tyr | Gly | Gly | Phe | | X⁷ |
|---|---|---|---|---|---|---|
| BOC | . Tyr ― | Gly —1— | Gly ― | Phe . OH | H . | X⁷ . OR |
| BOC | . Tyr ― | Gly —2— | Gly ― | Phe ――― | | X⁷ . OR |
| H | . Tyr ― | Gly —3— | Gly ― | Phe ――― | | X⁷ . OH |

—OR could be conveniently chosen from such residues as -OMe; -OEt; OBuᵗ; -OBzl; OBzl(p-NO₂) etc. depending on the ultimate choice of the manner of deprotection. With -OMe and -OEt, the carboxyl group could be liberated by alkaline saponification; with -OBuᵗ by mild acidolysis e.g. with trifluoroacetic acid or N-hydrogen chloride in acetic acid; with -OBzl or -OBzl(p-NO₂) by hydrogenolysis.

Step (A)

The general method of preparation of

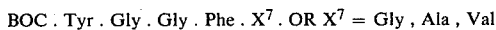

BOC . Tyr . Gly . Gly . Phe . X⁷ . OR  X⁷ = Gly , Ala , Val

R = Me

BOC.Tyr.Gly.Gly.Phe.OH (0.92 mmol.), HCl H.X⁷.OMe (e.g. glycine methyl ester hydrochloride (0.92 mmol.) and HOBT (1.84 mmol.) were dissolved in DMF (5 ml.) and NMM (0.92 mmol.) added. The mixture was cooled to −10° C. and DCCI (0.92 mmol.) added. The solution was allowed to warm slowly to ambient temperature and stirred overnight. The DCU was filtered, washed with a little DMF and the filtrate evaporated in vacuo. The residue was dissolved in ethyl acetate and washed successively with 5% aq. NaHCO₃; H₂O; 5% citric acid; H₂O. The solution was dried (MgSO₄), evaporated and the residue crystallised from an appropriate solvent.

| X⁷ | m.p. (cryst. solvent) | Rf | [α]$_D^{25}$ | Elemental Analysis | Amino Acid Analysis |
|---|---|---|---|---|---|
| Gly | 108–110° MeOH/ EtOAc/pe | 0.97³; 0.95⁴; 0.85⁵ | +1.37° (C = 0.5, MeOH) | C₃₀H₃₉N₅O₉ . H₂O: C, 57.05; H, 6.50; N, 11.09 Found : C, 57.02; H, 6.62; N, 10.64% | Gly (3.08); Tyr (1.00); Phe (1.05) |
| Ala | 115–117° EtOAc | 0.87³; 0.95⁴; 0.91⁵ | −8.81° (C = 0.5, in MeOH) | C₃₁H₄₁N₅O₉ : C, 59.32; H, 6.58; N, 11.16 Found : C, 59.19; H, 7.06; N, 10.74% | Gly(1.98); Ala(1.09); Tyr(1.00); Phe(1.03) |
| Val | 150–151° Pr/EtOAc/ Pr₂O | 0.97³; 0.95⁵ | −6.08° (0 = 0.5, in MeOH) | C₃₃H₄₅N₅O₉ : C, 60.44; N, 6.92; N, 10.68 Found : C, 59.94; H, 7.02; N, 10.37% | Gly(1.97); Val(0.94); Tyr(1.00); Phe(0.999) |

Step (B)

The general method of preparation of
BOC.Tyr.Gly.Gly.Phe.$X^7$.OH $X^7$=Gly,Ala,Val The protected pentapeptide BOC.Tyr.Gly.Gly.Phe.$X^7$.OMe was dissolved in methanol (6 ml.), water (3 ml.) was added and the pH maintained at 11.5 to 12.0 with N.NaOH until the theoretical amount of alkali had been added. The solution was concentrated in vacuo to remove methanol, diluted with water. Traces of insoluble material were filtered, the solution extracted with ethyl acetate to remove any residual ester and the aqueous phase brought to pH3 with 0.7M citric acid solution. The precipitated peptide was extracted into ethyl acetate. The extract was washed with water, dried with $MgSO_4$ and concentrated in vacuo.

-$NH_2$: amide
-NHEt: ethylamide

In Example 10, BOC.Tyr.Gly.Gly.Tyr.Leu.OBu was dissolved in methanol/methylene dichloride containing a few drops of borontrifluoride etherate. An excess of an ethereal solution of diazomethane was added and the solution allowed to stand at ambient temperature until its reaction with Pauly's reagent was negative. The solution was evaporated and the BOC and Bu protecting groups removed from the residual solid by means of N-hydrogen chloride in acetic acid in the presence of anisole in the normal manner. The peptide hydrochloride was isolated as a colourless amorphous powder after lyophilisation from aqueous solution.

In Example 21, the product peptide was purified by

| $X^7$ | | Rf | Elemental Analysis | |
|---|---|---|---|---|
| Gly | Amorphous | $0.84^3$; | $C_{29}H_{37}N_5O_9 \cdot H_2O$ : | C, 56.40; H, 6.32; |
|  | ppt. from EtOAc | $0.74^4$; |  | N, 11.34 |
|  | with pe | $0.83^5$ |  | Found : C, 56.33; H, 6.41; |
|  |  |  |  | N, 11.07% |
| Ala | Amorphous | $0.80^3$; | $C_{30}H_{39}N_5O_9 \cdot H_2O$ : | C, 57.05; H, 6.50; |
|  | ppt. from EtOAc | $0.66^4$; |  | N, 11.09; |
|  | with $Pr_2O$ | $0.87^5$ |  | Found : C, 57.20; H, 6.43; |
|  |  |  |  | N, 10.67% |
| Val | Amorphous | $0.88^3$; | $C_{32}H_{43}N_5O_9$ : | C, 59.89; H, 6.75; |
|  | ppt. from EtOAc | $0.85^4$; |  | Found : C, 59.98; H, 6.50% |
|  | with pe | $0.93^5$ |  |  |

Step (C) The general method of preparation of H.Tyr.Gly.Gly.Phe.$X^7$.OH HCl. $X^7$=Gly,Ala,Val To the pentapeptide BOC.Tyr.Gly.Gly.Phe.$X^7$.OH (100 mg.) was added 1. ON hydrogen chloride in acetic acid (5 ml.) and anisole (1 ml.). After stirring at ambient temperature for 90 mins. the solvents were removed in vacuo. Trituration of the residue with dry ether gave an amorphous solid. The product was dissolved in water, filtered and lyophilised to provide the hydrochloride salt of the peptide as a white solid.

chromatography on a column of silica gel (Merck) by elution with n-butanol: acetic acid: water (3:1:1). The Pauly-positive fractions with Rf: $0.44^2$ were combined, evaporated in vacuo and the residue lypophilised from aqueous solution.

The peptide base of Example 105 was prepared by reduction of the compound H.Tyr.Gly.Gly.Phe.Leu.OMe: the reducing agent was lithium aluminium hydride but other equivalent agents, common in the art, could also be used.

The peptide bases of Examples 111 and 112 were

| Ex. | $X^7$ | | Rf | $[\alpha]_D^{25}$ | Elemental Analysis | | Amino Acid Analysis |
|---|---|---|---|---|---|---|---|
| 1 | Gly | Amorphous | $0.82^3$; | +27.9° | $C_{23}H_{29}N_5O_7HCl \cdot H_2O$: | C,50.97; | Gly (3.02); |
|  | (HCl) | (lyophilised) | $0.63^4$; | (C = 0.18, |  | H,5.91; | Tyr (1.0); |
|  |  |  | $0.60^5$ | in MeOH) |  | N,12.93 | Phe (0.99) |
|  |  |  |  |  |  | Found: C,51.09; N,6.19; N,12.54% |  |
| 2 | Ala | Amorphous | $0.50^3$; | +22.3° | $C_{24}H_{31}N_5O_7 \cdot HCl \cdot H_2O$: | C,51.85; | Gly (1.95); |
|  | (HCl) | (lyophilised) | $0.58^4$; | (C = 0.2, |  | H,6.12; | Ala (1.01); |
|  |  |  | $0.67^5$ | in MeOH) |  | N,12.60 | Tyr (1.00); |
|  |  |  |  |  |  | Found: C,52.14; H,6.20, N,12.10% | Phe (0.98) |
| 3 | Val | Amorphous | $0.80^2$; | +31.7 | $C_{27}H_{35}N_5O_7 \cdot HCl \cdot 2H_2O$: | C,52.80; | Gly (2.1); |
|  | (HCl) | (lyophilised) | $0.67^4$; | (C = 0.1, |  | H,6.52; | Val (1.02); |
|  |  |  | $0.79^5$ | in MeOH |  | N,11.40 | Tyr (1.00); |
|  |  |  |  |  |  | Found: C,52.89; H,6.45; N,11.26% | Phe (1.05) |

The following peptides were prepared, with the characterising data respectively shown therefor, according to standard procedures in peptide chemistry analogous to those set out in the foregoing Examples and Reference Preparations. C-Terminal derivatives are indicated according to convention, that is to say:

-OMe: methyl ester prepared by (a) preparing Z-leucineamide from the protected amino acid; (b) converting the amide to the nitrile (phosphorus oxychloride); (c) preparing the protected leucine tetrazole by reacting the nitrile with hydrazoic acid; (d) deprotecting the leucyl amino function by hydrogenolysis (10% palladium on charcoal); (e) assembling the pentapeptide in the customary manner.

| Ex. No. | Compound | Rf | $[\alpha]_D^{25}$ (in methanol) |
|---|---|---|---|
| 4 | H.Tyr.D-Ala.Gly.Phe.Leu.OH HCl | 0.63² | +19.8° (c = 0.5) |
| 5(a) | H.Tyr.D-Ala.Gly.Phe.Met.OH HCl | 0.62²; 0.60³ | +17.2° (c = 0.5) |
| 5(b) | H.Tyr.D-Ala.Gly.Phe.Met.OMe | 0.67²; 0.70³ | +10.4° (c = 0.5) |
| 6 | H.Tyr.D-Ala.Ala.Phe.Leu.OH HCl | 0.65²; 0.56⁴ | +1.68° (c = 0.5) |
| 7 | H.Tyr.Gly.Gly.Tyr.Leu.OH HCl | 0.47²; 0.50³ | +24.4° (c = 0.54) |
| 8 | H.Phe.Gly.Gly.Tyr.Leu.OH HCl | 0.55²; 0.57⁴ | +26.45° (c = 0.54) |
| 9 | Me<br>\|<br>H.Tyr.Gly.Gly.Phe.Leu.OH HCl | 0.58²; 0.62⁴ | +21.77° (c = 0.5) |
| 10 | Me   Me<br>\|    \|<br>H.Tyr.Gly.Gly.Tyr.Leu.OH | 0.64²; 0.92³ | +21.0° (c = 0.51) |
| 11 | H.Tyr.Gly.D-Ala.Phe.Leu.OH HCl | 0.60²; 0.90²; 0.63⁴ | +36.67° (c = 1) |
| 12 | H.Tyr.Ala.D-Ala.Phe.Leu.OH HCl | 0.60²; 0.94³; 0.55⁴ | +6.43° (c = 1) |
| 13 | H.Tyr.Gly.Gly.Phe.Met.Thr.OH HCl | 0.72¹;0.63³;0.60⁴;0.60⁵ | |
| 14 | H.Tyr.D-Ala.Gly.Phe.Met.Thr.OH HCl | 0.10¹; 0.49²; 0.68³ | +12.46° (c = 0.52) |
| 15 | H.Arg.Tyr.Gly.Gly.Phe.Leu.OH 2HCl | 0.38²; 0.61⁴ | +17.7° (c = 0.52) |
| 16 | H.Tyr.Ala.D-Ala.Phe.Met.OMe HCl | 0.58²; 0.97³; 0.88⁴ | −3.66° (c = 0.2) |
| 17 | H.Tyr.Gly.D-Ala.Phe.Met.OMe HCl | 0.61²; 0.98³; 0.85⁴ | +30.19° (c = 0.2) |
| 18 | H.Tyr.Ala.D-Ala.Phe.Met.OH HCl | 0.58²; 0.54³; 0.61⁴ | +4.22° (c = 1) |
| 19 | H.Tyr.Gly.D-Ala.Phe.Met.OH HCl | 0.50²; 0.55³; 0.56⁴ | +34.19° (c = 1) |
| 20 | H.Arg.Tyr.Gly.Gly.Phe.Leu.Thr.OH 2HCl | 0.16²; 0.32³; 0.51⁴ | +1.63° (c = 0.5) |
| 21 | H.Tyr.D-Ala.Gly.Phe.Pro.OH HCl | 0.44³ | −1.52° (c = 0.51) |
| 22 | H.Tyr.D-Ala.D-Ala.Phe.Leu.OH HCl | 0.68²; 0.93³; 0.93⁴ | +43.71° (c = 1) |
| 23 | H.Tyr.D-Ala.Gly.Leu.Leu.OH HCl | 0.68²; 0.74³; 0.88⁴ | −4.43° (c = 0.5) |
| 24 | H.Tyr.Ile.Asn.Met.Leu.OH | 0.57²; 0.83⁴ | −13.5° (c = 0.2) |
| 25 | H.Tyr.Ala.Gly.Phe.Leu.OH HCl | 0.55²; 0.84³; 0.86⁴ | −1.35° (c = 1) |
| 26 | H.Tyr.Gly.Gly.Phe.Mle.OH HCl | 0.58²; 0.85³; 0.86⁴ | +24.44° (c = 0.4) |
| 27 | H.Tyr.D-Leu.Gly.Phe.Leu.OH HCl | 0.85¹; 0.86²; 0.79³ | +17.3° (c = 0.2) |
| 28 | H.Tyr.Ala.Ala.Phe.Leu.OH HCl | 0.76¹; 0.62²; 0.74³ | −33.6° (c = 0.6) |
| 29 | H.Tyr.Gly.Pro.Phe.Leu.OH HCl | 0.76¹; 0.68²; 0.75³ | −30.0° (c = 0.5) |
| 30 | H.Tyr.D-Ala.Gly.D-Phe.Leu.OH HCl | 0.57²; 0.86³ | +27.2° (c = 0.5) |
| 31 | H.Tyr.Gly.Gly.Phe.D-Leu.OH HCl | 0.71¹; 0.49²; 0.79³ | +28.7° (c = 0.4) |
| 32 | H.Tyr.Gly.Gly.D-Phe.Leu.OH HCl | 0.51²; 0.85³; 0.48⁴ | +24.5° (c = 0.52) |
| 33 | H.Tyr.Gly.Gly.Phe.Ile.OH HCl | 0.76¹; 0.85²; 0.65³ | +22.7°: (c = 0.6) |
| 34 | H.Tyr.D-Ala.Gly.C-Phenylglycyl.Leu.OH HCl | 0.64²; 0.85³ | +43.7° (c = 0.48) |
| 35 | H.Phe.D-Ala.Gly.Phe.Leu.OH HCl | 0.66²; 0.93³ | +21.2° (c = 0.52) |
| 36 | H.Tyr.D-Ala.Sar.Phe.Leu.OMe HCl | 0.64²; 0.90⁴ | +3.69 (c = 0.4) |
| 37 | H.Tyr.Gly.Ala.Phe.Leu.OH HCl | 0.62²; 0.86³; 0.65⁴ | −12.07° (c = 1) |
| 38 | H.Tyr.D-Ala.Gly.Phe.Thr.OH HCl | 0.50²; 0.51⁴ | +19.8° (c = 0.51) |
| 39 | H.Tyr.D-Ala.Asn.Phe.Leu.OH HCl | 0.55¹; 0.89³; 0.69⁴ | +6.26° (c = 0.49) |
| 40 | H.Tyr.D-Ala.Gly.Phe.D-Leu.OMe HCl | 0.63²; 0.92⁴ | +39.6° (c = 0.51) |
| 41 | H.Tyr.D-Ala.Gly.Phe.D-Leu.OH HCl | 0.57²; 0.93³; 0.82⁴ | +31.5° (c = 0.53) |
| 42 | Ac<br>\|<br>H.Tyr.D-Ala.Gly.Phe.Leu.OH HCl<br>Ac<br>\|<br>—Tyr— = O⁴'—acetyltyrosyl | 0.60²; 0.94³; 0.85⁴ | +14.6° (c = 0.5) |
| 43 | H.Tyr.D-Ala.Sar.Phe.Leu.OH HCl | 0.58²; 0.85⁴ | +9.89° (c = 1) |
| 44 | H.Tyr.D-ala.Gly.Phe.Leu.Thr.OH HCl | 0.55²; 0.93³; 0.72⁴ | +5.15° (c = 0.5) |
| 45 | H.MeTyr.Gly.Gly.Phe.Leu.OH HCl | 0.57²; 0.64³; 0.64⁴ | +25.5° (c = 0.5) |
| 46 | H.Tyr.D-Ala.Gly.Phe.Nle.OH HCl | 0.62²; 0.68⁴ | +23.2° (c = 1.0) |
| 47 | H.Tyr.Gly.Sar.Phe.Leu.OMe HCl | 0.56²; 0.70³; 0.90⁴ | +10.2° (c = 0.4) |
| 48 | H.D-Tyr.D-Ala.Gly.Phe.Leu.OH HCl | 0.55²; 0.68³ | −20.7° (c = 0.5) |
| 49 | H.D-Tyr.D-Ala.Gly.Phe.D-Leu.OH HCl | 0.57²; 0.62³; 0.50⁴ | −4.51° (c = 0.5) |
| 50 | H.Tyr.Gly.Sar.Phe.Leu.OH HCl | 0.59²; 0.80³; 0.68⁴ | +17.1° (c = 1.0) |
| 51 | H.Tyr.D-Ala.Gly.Phe.D-Leu.Thr.OH HCl | 0.51²; 0.66³; 0.55⁴ | +51.5° (c = 0.52) |
| 52 | H.Tyr.D-Ala.Gly.Phe.D-Met.OH HCl | 0.55²; 0.67³; 0.58⁴; 0.82⁵ | +31.0° (c = 0.51) |
| 53 | H.Tyr.Pro.Gly.Phe.Leu.OH HCl | 0.92³; 0.76⁴; 0.66⁵ | −8.6° (c = 0.2) |
| 54 | H.Tyr.D-Ala.Gly.Phe.D-Met.Thr.OH HCl | 0.61²; 0.76³ | +47.8° (c = 0.51) |
| 55 | H.Tyr.Sar.Gly.Phe.Leu.OH HCl | 0.72³; 0.91⁴; 0.54² | +20.8° (c = 1.0) |
| 56 | H.Me Tyr.D-Ala.Gly.Phe.Leu.OH | 0.90⁴; 0.85³; 0.52² | |
| 57 | H.Tyr.Gly.D-Pro.Phe.Leu.OH HCl | 0.89⁴; 0.82³; 0.59² | +55.0° (c = 1.0) |
| 58 | H.Tyr.D-Ala.D-Pro.Phe.Leu.OH sodium salt | 0.74⁴; 0.81³; 0.74² | +43.2° (c = 1.0) |
| 59 | H.MeTyr.Gly.Gly.Phe.Leu.OMe HCl | 0.98⁴; 0.99³; 0.48² | +18.1°(c = 0.4) |
| 60 | H.MeTyr.D-Ala.Gly.Phe.Leu.OMe HCl | 0.91⁴; 0.89³; 0.63² | |
| 61 | H.Tyr.D-MeAla.Gly.Phe.D-Leu.OMe HCl | 0.91⁴; 0.85³; 0.60² | +61.3°(c= 0.39) |
| 62 | H.Tyr.D-MeAla.Gly.Phe.D-Leu.OH HCl | 0.68⁴; 0.72³; 0.62² | +49.9°(c = 0.45) |
| 63 | H.Tyr.D-Ala.Gly.PheI.Leu.OMe HCl | 0.95⁴; 0.95³; 0.63² | +11.6°(c = 0.44) |
| 64 | H.Tyr.D-Ala.Gly.Phe.D-MetI.OMe HCl | 0.94⁴; 0.93³; 0.57² | +37.8° (c = 0.38) |
| 65 | H.D-Tyr.Gly.Gly.Phe.Leu.OH HCl | 0.58² | −39.0° (c = 1.0) |
| 66 | H.MeTyr.D-Ala.Gly.Phe.D-Leu.OH HCl | 0.55²; 0.81³; 0.82⁴ | +40.9° (c = 1) |
| 67 | H.MeTyr.D-Ala.Gly.Phe.D-Leu.OMe HCl | 0.52²; 0.90³; 0.92⁴ | +54.7° (C ' 1) |
| 68 | H.DOPA.Gly.Gly.Phe.Leu.OH HCl<br>DOPA = 3,4-dihydroxyphenylalanyl | 0.49²; 0.85³ | +13.8° (c = 0.4) |
| 69 | H.Tyr.MeAla.Gly.Phe.D-Leu.OH HCl | 0.51²; 0.88³; 0.79⁴ | +17° (c = 1.0) |
| 70 | H.Tyr.D-Ala.Gly.Phe.D-Leu.D-Thr.OH HCl | 0.50² | +48.9° (c = 0.5) |
| 71 | H.D-Tyr.Gly.Gly.Phe.Leu.OMe HCl | 0.63²; 0.97³; 0.93⁴ | −42.7° (C = 0.1) |
| 72 | H.Tyr.MeAla.Gly.Phe.D-Leu.OMe HCl | 0.59² | +9.03° (c = 0.2) |
| 73 | H.Tyr.D-Ala.Gly.Phe.D-Leu.NHBt HCl | 0.61²; 0.93⁴; 0.61⁵ | +46.5° (C = 0.5) |
| 74 | H.MeTyr.D-Ala.Gly.Phe.D-Leu.NHBt HCl | 0.58²; 0.92³; 0.96⁴ | +50.0° (c = 1) |

-continued

| Ex. No. | Compound | Rf | $[\alpha]_D^{25}$ (in methanol) |
|---|---|---|---|
| 75 | Me-MeTyr.D-Ala.Gly.Phe.Leu.OH acetate | 0.54², 0.62³, 0.66⁴ | +39.2° (c = 0.4) |
| 76 | Me-MeTyr.Gly.Gly.Tyr.Leu.OH acetate | 0.35², 0.63³, 0.87⁴ | +31.3° (c = 0.4) |
| 77 | Me-M Tyr.Gly.Ala.Phe.Leu.OH HCl | 0.55², 0.66³, 0.80⁴ | +38.2° (c = 1.0) |
| 78 | Me-MeTyr.Gly.Phe.Leu.OH HCl | 0.45², 0.65³, 0.58⁴ | +52.4° (c = 1.0) |
| 79 | Me-MeTyr.D-Ala.Gly.Phe.Leu.OMe HCl | 0.45², 0.97³, 0.97⁴ | |
| 80 | Me-MeTyr.Gly.Gly.Phe.Leu.OMe HCl | 0.38², 0.92³, 0.96⁴ | |
| 81 | Me-MeTyr.D-Ala.Gly.Phe.D-Leu.OH HCl | 0.40², 0.86³, 0.78⁴ | +62.4° (c = 1.0) |
| 82 | Me-MeTyr.D-Ala.Gly.Phe.D-Leu.OMe HCl | 0.41², 0.75³, 0.96⁴ | +66.4° (c = 1.0) |
| 83 | Me-D-MeTyr.Gly.Gly.Phe.Leu.OH HCl | 0.36², 0.89³, 0.60⁴ | −67.4° (c = 0.5) |
| 84 | Me-MeTyr.D-MeAla.Gly.Phe.D-Leu.OH HCl | 0.33², 0.76³, 0.81⁴ | +58.4° (c = 0.2) |
| 85 | H.Tyr.Gly.Gly.Phe.Leu.Tyr.Gly.OH HCl | 0.86³, 0.84⁴ | −4.79° (c = 0.1) |
| 86 | H.Tyr.D-Ala.Gly.His.Leu.OH 2HCl | 0.26², 0.47³, 0.52⁴ | +20.8° (c = 1.0) |
| 87 | H.Tyr.D-Ala.Gly.Phe.D-Leu.Phe.Gly.OH HCl | 0.63² | +13.4° (c = 0.5) |
| 88 | H.Tyr.Gly.Gly.Phe.Met(O).OH HCl | 0.18², 0.56³, 0.51⁴ | +18.7° (c = 0.2) |
| 89 | H.Tyr.D-Ala.Gly.Phe.D-Leu.Lys.Lys.OH diacetate | 0.44³, 0.38⁴ | +12.0° (c = 0.5) |
| 90 | H.Tyr.D-Trp.Gly.Phe.Leu.OH sodium salt | 0.76², 0.84³ | −4.72° (c = 1.0) |
| 91 | Ac<br>\|<br>H.Tyr.D-Ala.Gly.Phe.D-Leu.Tyr.OH | 0.72², 0.67⁵ | +35.6° (c = 0.5) |
| 92 | H.Tyr.D-Trp.Gly.Phe.D-Leu.OH HCl | 0.76² | +16.58° (c = 2)* |
| 93 | H.Tyr.D-Ala.Gly.Phe.D-Leu.p-chlorophenyl ester HCl | 0.75², 0.69⁵ | +38.9° (c = 0.5) |
| 94 | H.Tyr.D-Ala.Gly.Phe(4Cl).D-Leu.OH HCl | 0.42⁴ᴬ | −4.56° (c = 0.1) |
| 95 | He<br>\|<br>H.Tyr.Gly.Gly.Tyr.Leu.OH HCl | 0.55², 0.93³, 0.79⁴ | +28.4° (c = 0.1) |

⁴ᴬ:chloroform:methanol: .880ammonia (120:90:5)
*In glacial acetic acid

| Ex. No. | Compound | Rf | $[\alpha]_D^{25}$ (in methanol) |
|---|---|---|---|
| 96 | H.Tyr.D-Ala.Gly.Phe(4Cl).D-Leu.OMe HCl | 0.65⁵ | +36.5° (c = 0.5) |
| 97 | H.Tyr.Gly.Gly.D-Leu.OMe HCl | 0.52⁵ | +40.0° (c = 0.5) |
| 98 | H.MeTyr.D-Ala.Gly.Phe.D-Leu.NH₂ HCl | 0.56² | +50.7° (c = 1) |
| 99 | H.Tyr.Gly.Gly.Phe.D-Met.OMe HCl | 0.62³, 0.64⁵ | +43.7° (c = 0.5) |
| 100 | H.Tyr.Gly.Gly.Phe.D-Met.OH HCl | 0.55², 0.51⁵ | +38.3° (c = 0.5) |
| 101 | H.MeTyr.D-Ala.Gly.Phe.D-Met.OMe HCl | 0.62², 0.75³, 0.92⁴ | +59.4° (c = 0.12) |
| 102 | H.Tyr.Asn.Gly.Phe.D-Met.OH | 0.52², 0.53³ᴬ | −11.8° (c = 0.52) |
| 103 | H.Tyr.Asn.Gly.Phe.D-Leu.OH | 0.48², 0.58³ᴬ | −21.0° (c = 0.5) |
| 104 | Me-MeTyr.MeAla.Gly.Phe.D-Leu.OH HCl | 0.43², 0.48³ | +13.8° (c = 0.1) |

*³ᴬ : chloroform:methanol: 32% acetic acid (120:90:5)

| Ex. No. | Compound | Rf | $[\alpha]_D^{25}$ (in methanol) |
|---|---|---|---|
| 105 | H.Tyr.Gly.Phe.O-acetylleucinol HCl<br>—O-acetylleucinol = —NH.CH(CH₂.CH(CH₃)₂).CH₂.O.CO.CH₃ | 0.81³, 0.84⁴, 0.68⁵ | |
| 106 | H.Tyr.Gly.Gly.Phe.leucinol HCl<br>-leucinol = —NH.CH(CH₂.CH(CH₃)₂).CH₂.OH | 0.81³, 0.75⁴, 0.68⁵ | |
| 107 | H.Tyr.Ala(αMe).Gly.Phe.D-Leu.OH HCl<br>—Ala(αMe)— = -NH.C(CH₃)₂.CO— | 0.55², 0.77³, 0.59⁴ | +25.4° (c = 0.52) |
| 108 | H.Tyr.Ala(αMe).Gly.Phe.D-Leu.OMe HCl | 0.70², 0.89³, 0.95⁴ | +28.3° (c = 0.5) |
| 109 | H.βHomoTyr.Gly.Gly.Phe.Leu.OH HCl | 0.53², 0.63³, 0.52⁴ | −3.14° (c = 0.5) |
| 110 | H.Tyr.D-Ala.Gly.Phe.D-βHomoLeu.OH HCl | 0.58¹, 0.82³, 0.49⁴ | +10.7° (c = 0.5) |
| 111 | H.Tyr.D-Ala.Gly.Phe.Leu-tetrazole HCl | 0.60², 0.92³, 0.96⁴ | +48.2° (c = 0.1) |
| 112 | H.Tyr.D-Ala.Gly.Ala.Phe.D-Leu-tetrazole HCL | 0.60², 0.90³, 0.94⁴ | +39.7° (c = 0.1) |

—Leu-tetrazole =

$$-NH-CH-C \overset{NH}{\underset{N}{\underset{\diagdown}{\underset{N}{\diagup}}}}N$$

with side chain CH(CH₃)₂–CH₂–

| Ex. No. | Compound | Rf | $[\alpha]_D^{25}$ (in methanol) |
|---|---|---|---|
| 113 | H.DOPA.D-Ala.Gly.Phe.D-Leu.OH HCl | 0.56², 0.72³ | +29.9° (c = 0.1) |
| 114 | H.D-DOPA.D-Ala.Gly.Phe.D-Leu.OH HCl | 0.58², 0.68³ | +9.8° (c = 0.1) |
| 115 | H.MeTyr.D-Ala.Gly.Phe.D-Met.NHEt HCl | 0.59², 0.84³, 0.90⁴ | +59.7° (c = 1) |
| 116 | H.MeTyr.D-Ala.Gly.Phe.D-Metl.OH HCl | 0.52², 0.71³, 0.69⁴ | +34.7° (c = 1) |
| 117 | H.MeTyr.D-Ala.Gly.Phe.D-Met.NH₂ HCl | 0.52², 0.72³, 0.85⁴ | +48.9° (c = 1) |
| 118 | H.Phe(4Cl).D-Ala.Gly.Phe.D-Leu.OH acetate | 0.65³ᴬ, 0.45⁴ᴬ | −0.78° (c = 0.2) |
| 119 | H.Tyr.D-Ala.Gly.Phe(4Cl).D-Leu.NHEt HCl | 0.63², 0.68³ᴬ, 0.68⁵ | +40.7° (c = 0.5) |
| 120 | Me<br>\|<br>H.Tyr.Gly.Gly.Tyr.Leu.OMe HCl | 0.62², 0.96³, 0.15⁶ | +18.9° (c = 1) |

³ᴬ,⁴chloroform: methanol: 32% acetic acid (120:90:5)
⁴ᴬ: chloroform: methanol: .380 ammonia (120:90:5)

Pharmaceutical Formulations

(A) Tablet Formulation (20 mg/tablet)

| | |
|---|---|
| Compound of formula (I) | 20 mg |
| Lactose | 76 mg |
| Maize Starch | 10 mg |
| Gelatin | 2 mg |
| Magnesium Stearate | 2 mg |

Mix together the compound of formula (I), Lactose and Maize Starch. Granulate with a solution of the Gelatin dissolved in water. Dry the granules, add the Magnesium Stearate and compress to produce tablets, 110 mg per tablet (B) Suppository (5 mg/product)

| Compound of formula (I) | 250 mg |
| Suppository Base (Massa Esterinum C) | to 100 g |

Melt the suppository base at 40° C. Gradually incorporate the compound of formula (I) in fine powder form and mix until homogeneous. Pour into suitable moulds, 2 g per mould, and allow to set.

Massa Esterinum C is a commercially available suppository base consisting of a mixture of mono, di, and tri glycerides of saturated vegetable fatty acids. It is marketed by Henkel International, Dusseldorf.

(C) Pessary (5 mg/product)

| Compound of formula (I) | 5 mg |
| Lactose | 400 mg |
| Providone | 5 mg |
| Magnesium Stearate | 5 mg |

Mix together the compound of formula (I) and Lactose. Granulate with a solution of Povidone in 50% aqueous ethanol. Dry the granules add the Magnesium Stearate and compress on suitably shaped punches, 415 mg per pessary.

(D) Freeze-dried Injection 100 mg/vial

| Compound of formula (I) | 100 mg |
| Water for Injections to | 2.0 ml |

Dissolve the compound of formula (I) in the Water for Injections. Sterilise the solution by passage through a membrane filter, 0.2 μm pore size, collecting the filtrate in a sterile receiver. Fill into sterile glass vials, 2 ml/vial under aseptic conditions and freeze-dry. Close the vials with sterile rubber closures secured with an aluminium seal.

The injection is reconstituted prior to administration by the addition of a convenient volume of Water for Injections or sterile saline solution.

In the foregoing, the weight of the compound of formula (I) is in each instance calculated with reference to the peptide base.

EXAMPLE

The compounds were examined for their ability to inhibit neurally evoked contractions of the isolated mouse vas deferens preparation (method of Hughes et al, *Brain Research*, 88 (1975) 296, using pulses at 0.1 Hz). The concentration of the test compound in the organ bath was successively increased at intervals of ten contractions until either the contractions had decreased to less than 30% of the resting contraction height or the final bath concentration of the test compound had reached a minimum of $10^{-4}M$.

Reversal of the inhibition of the contractions was effected for morphine and each test compound by addition to the bath, before the final washout, of the known narcotic antagonist naloxone (1-N-allyl-7,8-dihydro-14-hydroxynormorphinone).

The heights of the five contractions that immediately preceded the addition of the first "dose" of test compound were measured and their mean calculated. The resultant mean contraction associated with a particular bath concentration of test compound was calculated from the heights of the 6th, 7th, 8th, 9th and 10th contractions after the addition of the appropriate "dose" of test compound, i.e. the five contractions that immediately preceded the subsequent "dose" or washout.

The mean control contraction height and the concentration related mean contraction heights were used to compute the constants in an equation based on the Langmuir Adsorption Isotherm which defined the dose response curve:

$$y = \frac{C1 + C2 \cdot C3 \cdot x}{1 + C3 \cdot x}$$

where
y = contraction (mm)
x = dose
C1 = maximum predicted contraction of tissue
C2 = minimum predicted contraction of tissue
C3 = absolute potency For each test compound the D50 was calculated, defined as the dose giving the resonse that is halfway between the maximum response and the minimum contraction of the tissue.

Potency relative to morphine was calculated from the following formula:

RP = antilog[logD50(MORPHINE)-logD50(TEST COMPOUND)]

Generally at least two cumulative dose response curves were constructed and a mean D50 calculated. The significance of the difference between the D50 values for morphine and the test compound was assessed by Student's T-test using the logD50 values.

The results are as shown in the following table:

| Compound of Ex. No. | Mean D50 ($\times 10^{-6}$) | Relative Potency (Morphine) |
| --- | --- | --- |
| Morphine | 0.466 | 1.0 |
| 4 | 0.00174 | 267 |
| 5(a) | 0.00203 | 229 |
| 5(b) | 0.00495 | 94 |
| 14 | 0.00203 | 229 |

What we claim is:
1. A compound of the formula:

H.Tyr.Gly.Gly.Phe.X$^7$.OR wherein:
X$^7$ is selected from the group consisting of Ile, Nle, Pro, Val, Ala, NVa, D-Leu and D-Met;
R is lower alkyl of 1 to 6 carbon atoms;
and the stereochemical configuration of the Tyr and Phe residues may independently be D, L or DL.

2. A compound according to claim 1 or a salt, ester, amide, N-alkylamide or N,N-alkylamide or a pharmaceutically acceptable acid addition salt thereof.

3. A pharmacologically and pharmaceutically acceptable salt or acid addition salt of a compound or derivatives thereof according to claim 1.

4. A compound according to claim 1 wherein X$^7$ is D-Leu and R is methyl, or a salt, ester, amide, N-alkylamide or N,N-dialkylamide, thereof, or a pharmaceutically acceptable acid addition salt thereof.

5. A compound according to claim 1 wherein $X^7$ is D-Met and R is methyl, or a salt, ester amide, N-alkylamide or N,N-dialkyamide thereof, or a pharmaceutically acceptable acid addition salt thereof.

6. A pharmaceutical formulation for obtaining a morphine-like effect comprising a pharmaceutically acceptable carrier and an effective morphine-like treatment amount of a compound of the formula:

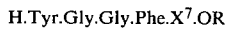

H.Tyr.Gly.Gly.Phe.X$^7$.OR or a pharmacologically and pharmaceutically acceptable salt, ester, amide, N-alkylamide or N,N-dialkylamide thereof, or a pharmacologically and pharmaceutically acceptable acid addition salt thereof, wherein:
$X^7$ is selected from the groups consisting of Ile, Nle, Pro, Val, Ala, NVa, D-Leu and D-Met;
R is lower alkyl of 1 to 6 carbon atoms; and
the stereochemical configuration of the Tyr and Phe residues may independently be D, L or DL.

7. The formulation of claim 6 which comprises a pharmacologically and pharmaceutically acceptable ester of said peptide or a pharmacologically and pharmaceutically acceptable acid addition salt thereof.

8. The formulation of claim 6 which comprises a pharmacologically and pharmaceutically acceptable amide of said peptide or a pharmacologically and pharmaceutically acceptable acid addition salt thereof.

9. The formulation of claim 6 which comprises a pharmacologically and pharmaceutically acceptable N-alkylamide or N,N-diakylamide of said peptide or a pharmacologically and pharmaceutically acceptable acid addition salt thereof.

10. The formulation of claim 6, suitable for administration by a route selected from oral, rectal, nasal, buccal, vaginal and parenteral.

11. The formulation of claim 6, suitable for administration by a route selected from oral, rectal, vaginal and parenteral.

12. The formulation of claim 6 which comprises the peptide or derivative thereof, or acid addition salt thereof, in solution in an aqueous medium.

13. The formulation of claim 6 in unit dosage form.

14. The formulation of claim 13 wherein each unit dosage contains the peptide or derivative thereof, or acid addition salt thereof, in an amount in the range 0.125 μg. to 2g., calculated with reference to the peptide base.

15. The formulation of claim 6 in the form of a tablet suitable for oral administration.

16. The formulation of claim 6 wherein said compound is:

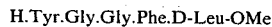

H.Tyr.Gly.Gly.Phe.D-Leu-OMe or a pharmacologically and pharmaceutically acceptable salt, ester, amide, N-alkylamide or N,N-dialkylamide thereof, or a pharmacologically and pharmaceutically acceptable acid addition salt thereof.

17. The formulation of claim 6 wherein said compound is:

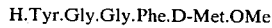

H.Tyr.Gly.Gly.Phe.D-Met.OMe or a pharmacologically and pharmaceutically acceptable salt, ester, amide, N-alkylamide or N,N-dialkylamide thereof, or a pharmacologically and pharmaceutically acceptable acid addition salt thereof.

18. A method for the treatment of a mammal for a condition therein an agent with a morphine-like effect is indicated, comprising the administration to the mammal of an effective morphine-like treatment, non-toxic amount of a peptide of the formula:

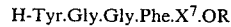

H-Tyr.Gly.Gly.Phe.X$^7$.OR or a pharmacologically and pharmaceutically acceptable salt, ester, amide, N-alkylamide or N,N-dialkylamide thereof, or a pharmacologically and pharmaceutically acceptable acid addition salt thereof, wherein
$X^7$ is selected from the group consisting of Ile, Nle, Pro, Val, Ala, NVa, D-Leu and D-Met;
R is lower alkyl of 1 to 6 carbon atoms;
and the stereochemical configuration of the Tyr and Phe residues may independently be D, L or DL.

19. The method of claim 18 which comprises administration of a pharmacologically and pharmaceutically acceptable ester of said peptide or a pharmacologically and pharmaceutically acceptable acid addition salt thereof.

20. The method of claim 18 which comprises administration of a pharmacologically and pharmaceutically acceptable amide of said peptide or a pharmacologically and pharmaceutically acceptable acid addition salt thereof.

21. The method of claim 18 which comprises administration of a pharmacologically and pharmaceutically acceptable N-alkylamide or N,N-dialkylamide of said peptide or a pharmacologically and pharmaceutically acceptable acid addition salt thereof.

22. The method of claim 18 which comprises administration by a route selected from oral, rectal, nasal, buccal, vaginal and parenteral.

23. The method of claim 18 which comprises administration by a route selected from oral, rectal, vaginal and parenteral.

24. The method of claim 18 for the relief of pain, for the suppression of cough, for the induction of constipation or for the treatment of diarrhea or dysentery.

25. The method of claim 18 wherein the peptide or derivative thereof, or acid addition salt thereof, is administered at a dosage in the range 0.0025 μg. to 40 mg per kilogram bodyweight of the mammal, calculated with reference to the peptide base.

26. The method of claim 18 wherein the mammal is man.

27. The method of claim 18 wherein said compound is:

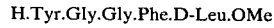

H.Tyr.Gly.Gly.Phe.D-Leu.OMe or a pharmacologically and pharmaceutically acceptable salt, ester, amide, N-alkylamide or N,N-dialkylamide thereof, or a pharmacologically and pharmaceutically acceptable acid addition salt thereof.

28. The method of claim 18 wherein said compound is:

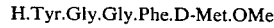

H.Tyr.Gly.Gly.Phe.D-Met.OMe or a pharmacologically and pharmaceutically acceptable salt, ester, amide, N-alkylamide or N,N-dialkylamide thereof, or a pharmacologically and pharmaceutically acceptable acid addition salt thereof.

* * * * *